(12) United States Patent
Bishop

(10) Patent No.: US 6,603,877 B1
(45) Date of Patent: Aug. 5, 2003

(54) METHOD OF AND APPARATUS FOR OPTICAL IMAGING INSPECTION OF MULTI-MATERIAL OBJECTS AND THE LIKE

(75) Inventor: Robert Bishop, Newton, MA (US)

(73) Assignee: Beltronics, Inc., Newton, MA (US)

( * ) Notice: Subject to any disclaimer, the term of this patent is extended or adjusted under 35 U.S.C. 154(b) by 0 days.

(21) Appl. No.: 09/323,441

(22) Filed: Jun. 1, 1999

(51) Int. Cl.$^7$ ................................................ G06K 9/00
(52) U.S. Cl. .................. 382/165; 382/205; 382/224; 382/100
(58) Field of Search ............... 382/165, 205, 382/224, 108, 228, 100, 141, 143, 145; 356/243.1–243.8, 239.3; 348/128, 131, 132

(56) References Cited

U.S. PATENT DOCUMENTS

| | | | | |
|---|---|---|---|---|
| 4,650,333 A | * | 3/1987 | Crabb et al. ............... 356/376 |
| 4,764,969 A | * | 8/1988 | Ohtombe et al. ............. 382/8 |
| 5,524,152 A | * | 6/1996 | Bishop et al. .............. 382/165 |
| 5,544,256 A | * | 8/1996 | Brecher et al. ............. 382/149 |
| 5,546,475 A | * | 8/1996 | Bolle et al. ................ 382/190 |
| 5,680,476 A | * | 10/1997 | Schmidt et al. ............. 382/159 |
| 5,801,965 A | * | 9/1998 | Takagi et al. ............... 364/552 |
| 5,818,964 A | * | 10/1998 | Itoh ........................... 382/205 |
| 5,969,753 A | * | 10/1999 | Robinson .................... 348/130 |
| 6,075,880 A | * | 6/2000 | Kollhof et al. ............. 382/141 |
| 6,075,891 A | * | 6/2000 | Burman ...................... 382/191 |
| 6,122,042 A | * | 9/2000 | Wunderman et al. ......... 356/73 |

* cited by examiner

Primary Examiner—Amelia M. Au
Assistant Examiner—Anand Bhatnagar
(74) Attorney, Agent, or Firm—Rines and Rines

(57) ABSTRACT

A novel method all of and apparatus for categorizing different material regions of an object-to-be inspected, by optical scanning of the object to produce a pixel image thereof, discriminating different pixel regions of the image corresponding to possibly different materials on the basis of color, and texture brightness measurements of the pixel regions and assigning preliminary likelihoods to such discrimination through with ambiguities; and comparing the measurements of the pixel regions with their local neighborhood surroundings in the image to assist in resolving said ambiguities and determining the material categorizations of the pixel regions with a high likelihood.

39 Claims, 17 Drawing Sheets

Likelihood Curves

Likelihood Curves for Two Characteristics

Likelihood Curves for Two Characteristics

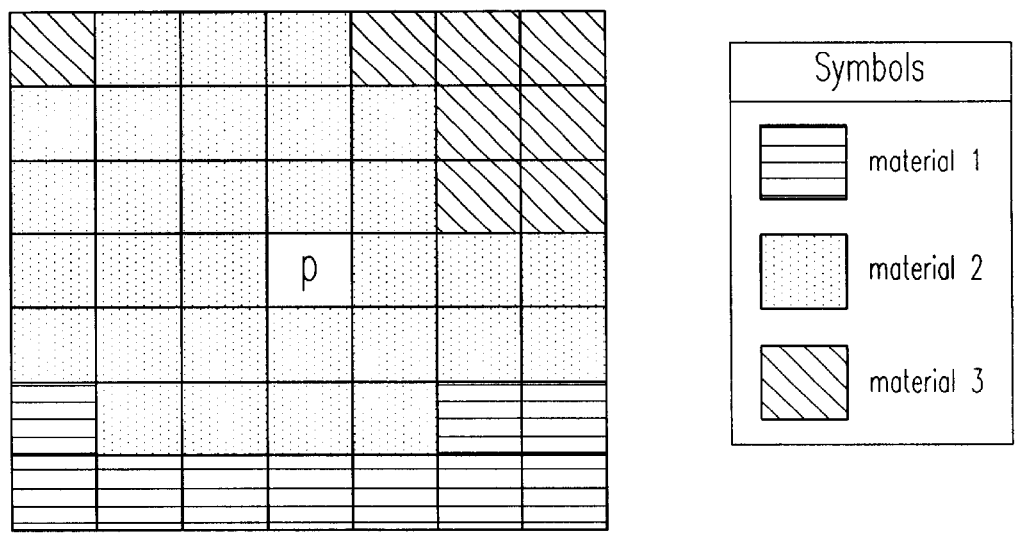
Comparison of Point to Neighbors
FIG. 3
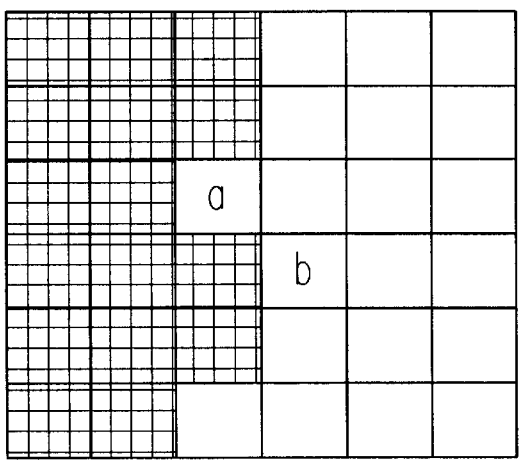
Area to be Filtered, with Pixels a and b
FIG. 4a
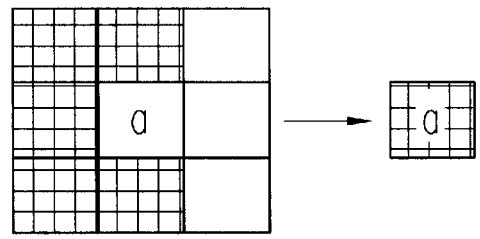
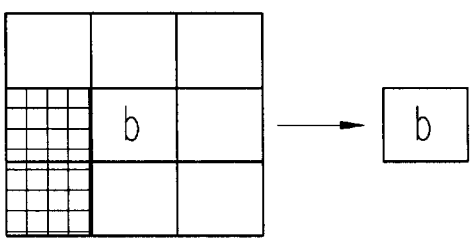
3x3 Filter Results for Pixels a and b
FIG. 4b
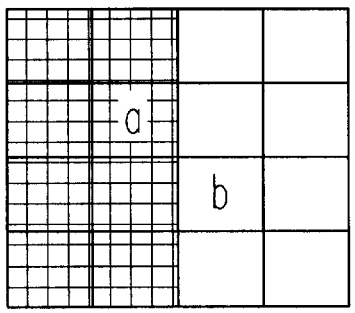
Area After Filtering
FIG. 4c
FIG. 4a-c Median Filter Analyzing Sharp Boundary

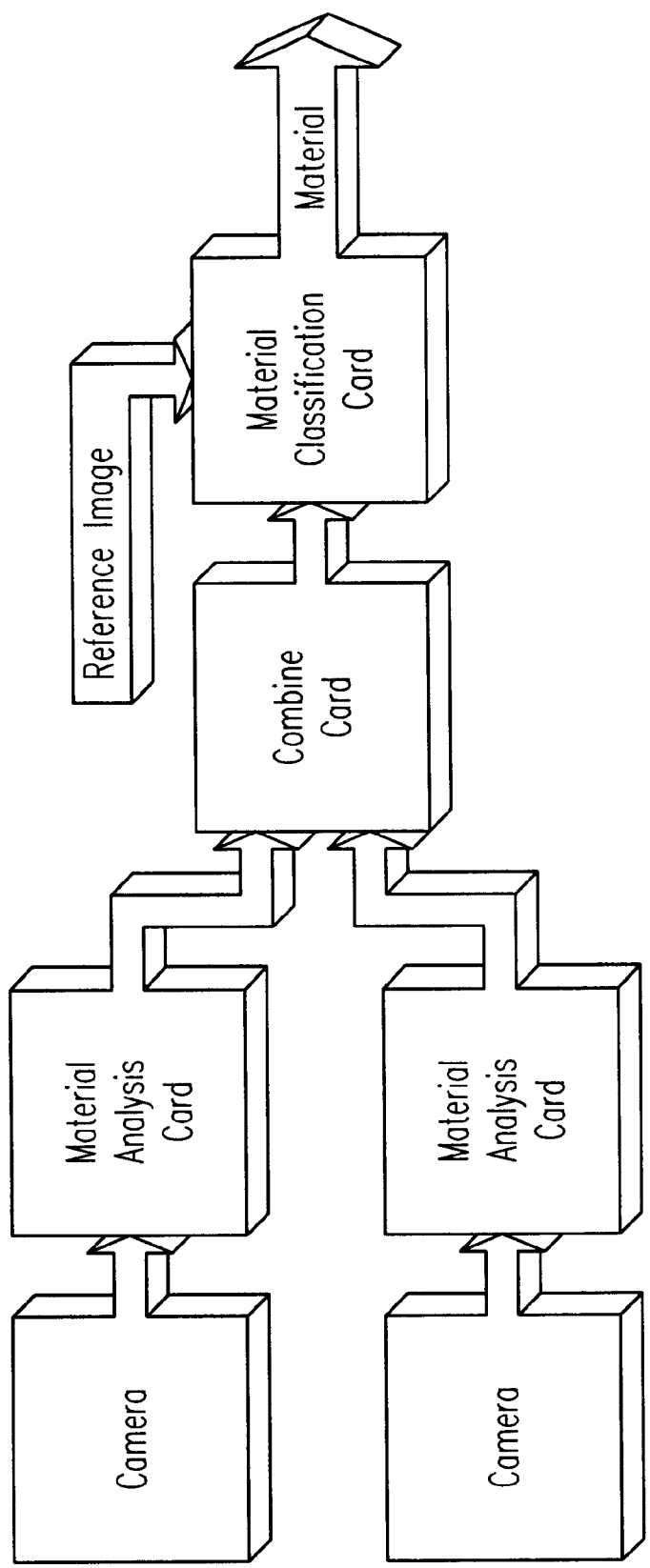
FIG. 5 General Architecture

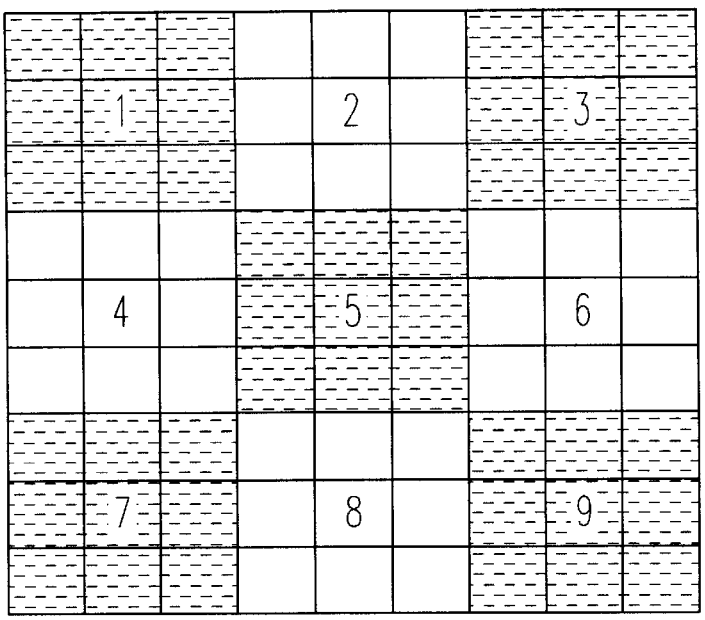

Spaced 9x9 median where each pixel is already the center of a previous 3x3 median followed by a second 7x7 median.

FIG. 6d

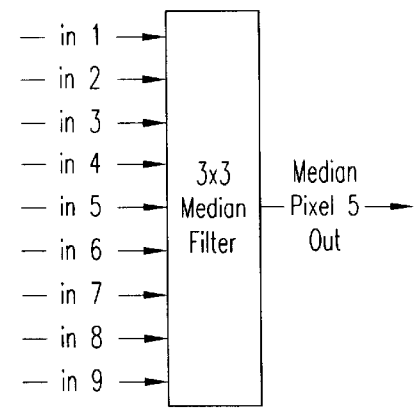

FIG. 6e

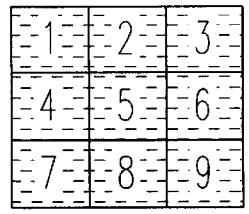

Normal 3x3 median where each pixel 5 is the center of the median.

FIG. 6a

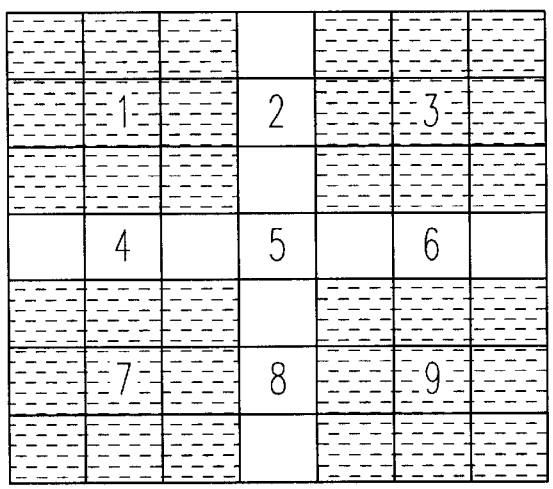

Spaced 7x7 median where each pixel is already the center of a previous 3x3 median followed by a second 5x5 median.

FIG. 6c

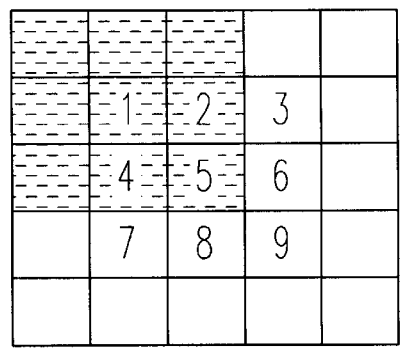

Spaced 5x5 median where each pixel is already the center of a previous 3x3 median followed by a second 3x3 median.

FIG. 6b

FIG. 6a–e Spaced Median Filter
FIG. 6a–d Spaced Median Filter Arrangement

Original Image

Image After 5x5 Filtering

Absolute Value of Difference

FIG. 8a-c Texture Calculation

Combine Card

Material Classification Card

FIG. 11a-b Smoothing Preliminary Likelihoods

Top metal pad focused on top surface, no transmitted light is in big mesh area-image present.

Top metal pad in big mesh area-image focused on bottom surface and holes illuminated using transmitted light.

Top metal pad in big mesh area-image focused halfway between top and bottom metal surfaces.

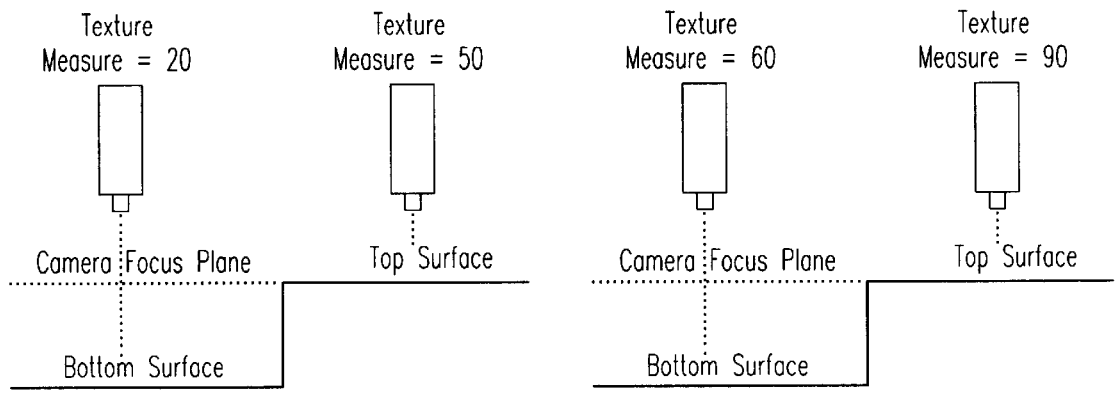
FIG. 15: Region A
FIG. 16: Region B
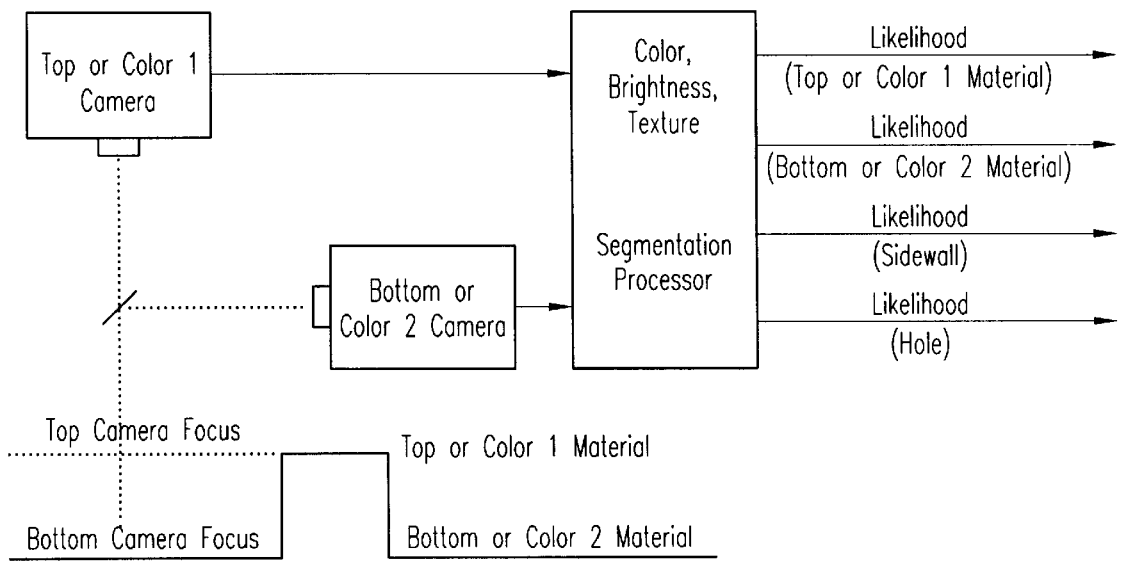
FIG. 17

Top metal pad in big mesh area—camera focused on top surface, no transmitted light.

Top metal likelihood image generated by segmenter. Intensity is proportional to likelihood.

Side wall likelihood image generated by segmenter. Intensity is proportional to likelihood.

Top metal pad in big mesh area—camera focused on bottom surface, with transmitted light to enable detection of holes.

Bottom metal likelihood image generated by segmenter. Likelihood is proportional to intensity.

Hole likelihood image generated by segmenter. Likelihood is proportional to intensity.

Initial segmented image for Figures 18 & 21

Certainty image for Figure 24

Ambiguity image for Fig. 24

METHOD OF AND APPARATUS FOR OPTICAL IMAGING INSPECTION OF MULTI-MATERIAL OBJECTS AND THE LIKE

FIELD

The present invention relates to the optical imaging and scanning inspection of objects (where the term "object" is used herein generically to connote any sample, surface or article-to-be-inspected) for identification of predetermined patterns therein, as for detecting manufacturing defects or other variations in such objects as, for example, electronic circuit boards or wafers or the like, and for determining different material regions of such objects more generally.

BACKGROUND

In connection with such electronic circuit boards, wafers, and similar objects, prior automatic optical image scanning inspection techniques have been successfully employed to detect such defects or variations, with differentiation between, for example, images of conductor and insulator materials, aided by brightness, color and other differences in the light reflected from the different materials, as described in U.S. Pat. No. 5,524,152 of common assignee herewith, and in U. S. Pat. No. 5,119,434.

As wafers and other composites become more complex and involve multilayers of varied material patterns, a greater degree of material discrimination has become essential. The present invention, accordingly, carries such different material categories in optical image inspection to a higher and more sophisticated and accurate level, involving using also local neighborhood comparisons about the various material regions that provide a high degree of likelihood of the correctness and lack of ambiguity of the material identification and characterization.

As before intimated, the optical image scanning inspection of objects requires determination of material regions therein; that is, for example, regions of metal conductor must be defined as different from regions of insulator, and unique types of each must be differentiated. In this way, each region can be processed correctly based on its material. A smooth metal surface can be checked for high-texture regions of contamination; but a textured metal will not necessarily be labeled contaminated. In accordance with the present invention, an imaged object comprising varied materials is categorized into given materials by discriminating several different image characteristics, such as color, texture, brightness, and average brightness (in a highly textured area), and also by observing how a small region compares to the local neighborhood around it.

OBJECTS OF INVENTION

A primary object of the present invention, thus, is to provide a new and improved method of and apparatus for optically imaging and scanning objects constituted of different materials, and for differentiating such materials through a novel material characterization technique that imbues likelihood values for the correct identification and distinguishment of the different materials.

Other and further objects will be explained hereinafter and are more particularly delineated in the appended claims.

SUMMARY

In summary, however, from one of its view points, the invention embraces a method of categorizing different material regions of an object-to-be-inspected, that comprises, optically scanning the object to produce a pixel image thereof; discriminating different pixel regions of the image corresponding to possibly different materials on the basis of color and brightness measurements of the pixel regions and assigning preliminary likelihoods to such discrimination though with ambiguities; comparing the pixel regions with their local neighborhood surroundings in the image, and preferably also with a reference image, to compare likelihoods and ambiguities of the pixel and its local neighborhood with the reference image, thereby to assist in resolving said ambiguities and to determine the materials categorization of the pixels with high likelihoods.

Preferred and best mode design and implementations will be detailed hereinafter.

DRAWINGS

The invention will now be described in connection with the accompanying drawings, FIG. 1 of which is an explanatory graph of likelihood versus reflection brightness from an illustrative three-material object;

FIG. 3 is a diagram illustrating a pixel point of the object image compared with three different neighboring material images surrounding the same;

Figure 7:
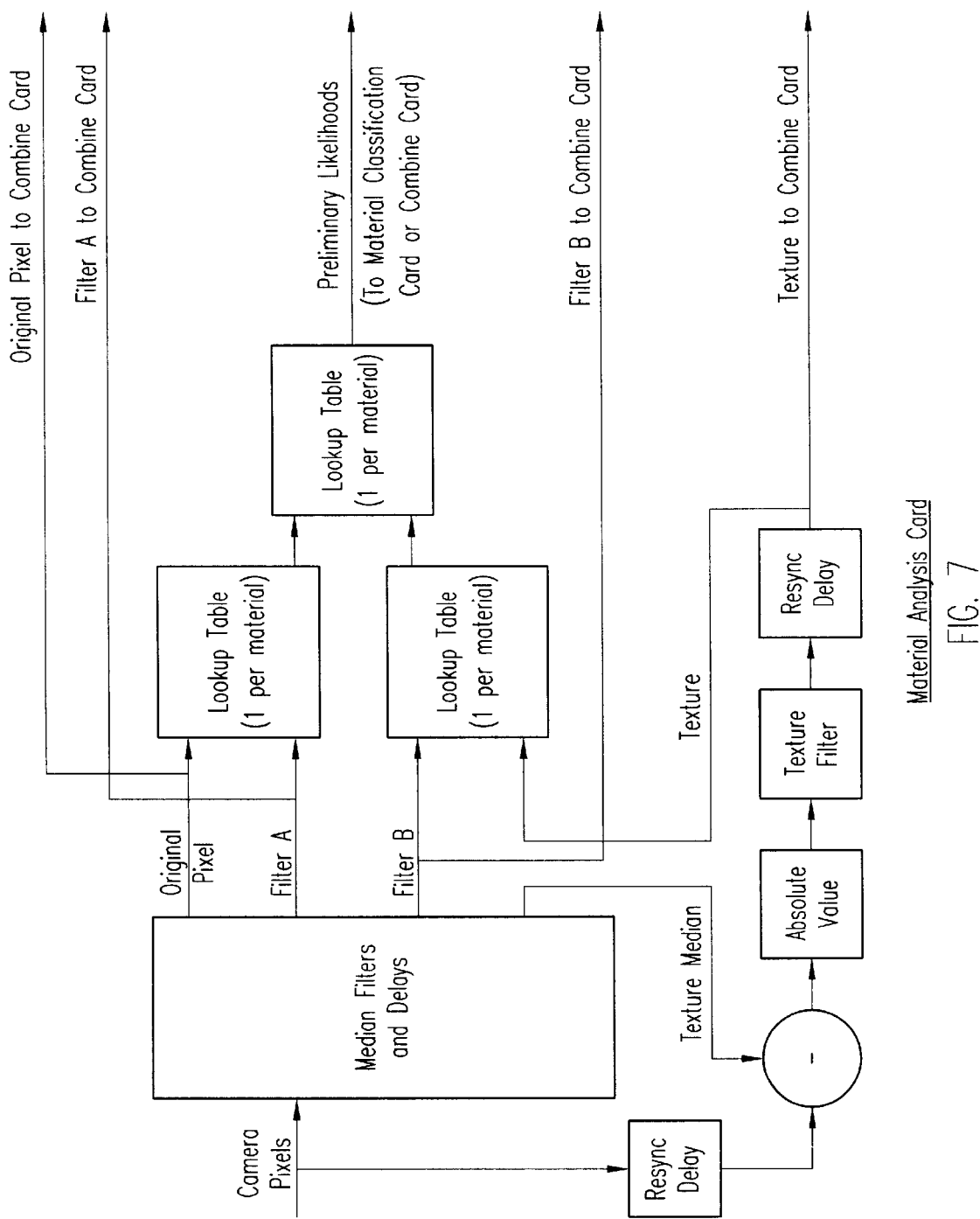
Figure 8A:
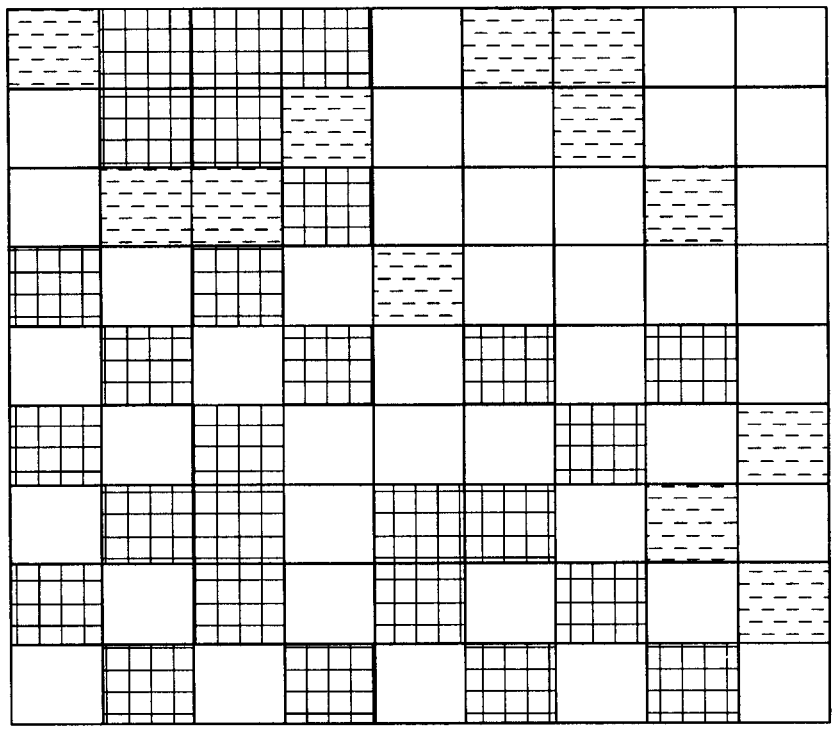
Figure 8B:
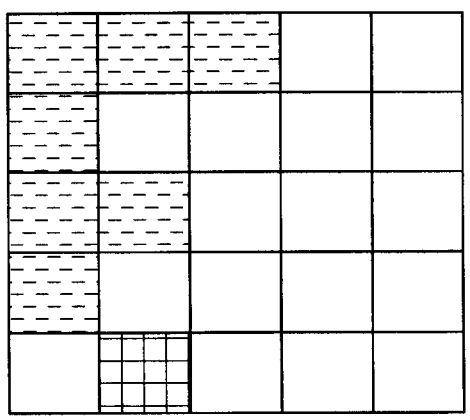
Figure 8C:
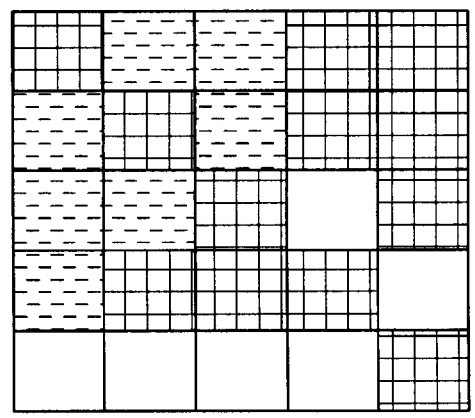
Figure 9:
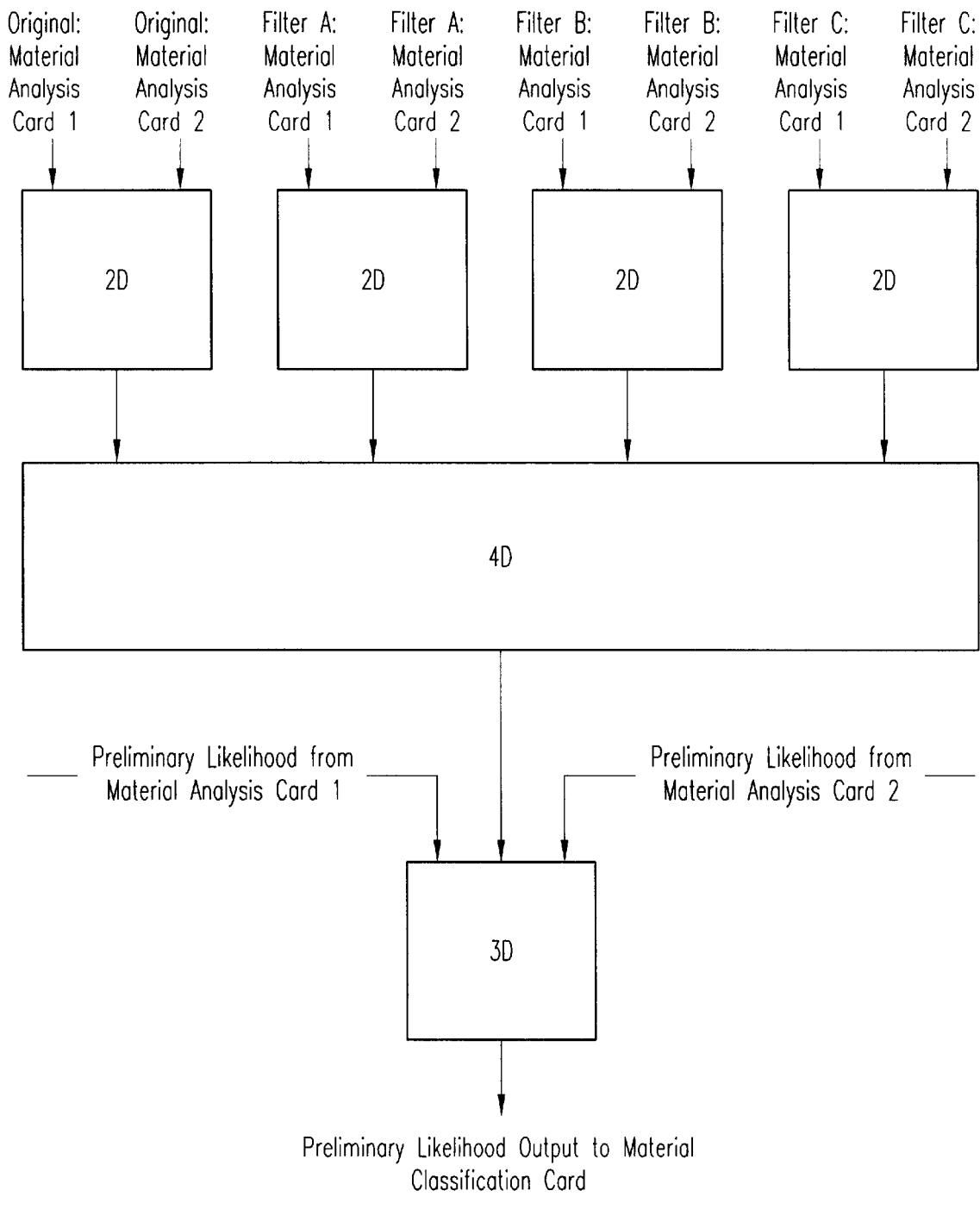

FIGS. 4(a)–(c) are diagrams of image pixel arrays representing median filter analysis of sharp boundaries, FIG. 4(a) depicting the area to be filtered containing pixels a and b; FIG. 4(b), 3×3 pixel matrixes representing filtering results for pixels a and b; and FIG. 4(c), the pixel matrix area after filtering;

FIG. 5 is a block and flow diagram of the general architecture of the system of the invention;

FIGS. 6(a)–(e) show spaced median filter operation, with FIG. 6(a) illustrating a normal 3×3 median matrix where pixel 5 is the center of the median; FIG. 6(b), a spaced 5×5 median where each pixel is already the center of a previous 3×3 median followed by a second 3×3 median; FIG. 6(c), a spaced 7×7 median where each pixel is already the center of a previous 3×3 median followed by a second 5×5 median; FIG. 6(d), a spaced 9×9 median where each pixel is already the center of a previous 3×3 median followed by a second 7×7 median; and FIG. 6(e) is a block diagram of the spaced median filter arrangement;

FIG. 7 is a block and circuit diagram of the material analysis type card useful with the system of the invention;

FIGS. 8(a)–(c) are pixel matrixes representing material region texture calculations wherein FIG. 8(a) shows an illustrative original image, FIG. 8(b), the image after 5×5 filtering, and FIG. 8(c) the absolute value of difference;

FIG. 9 is a diagram of a combine card useful in the system of the invention

Figure 10:
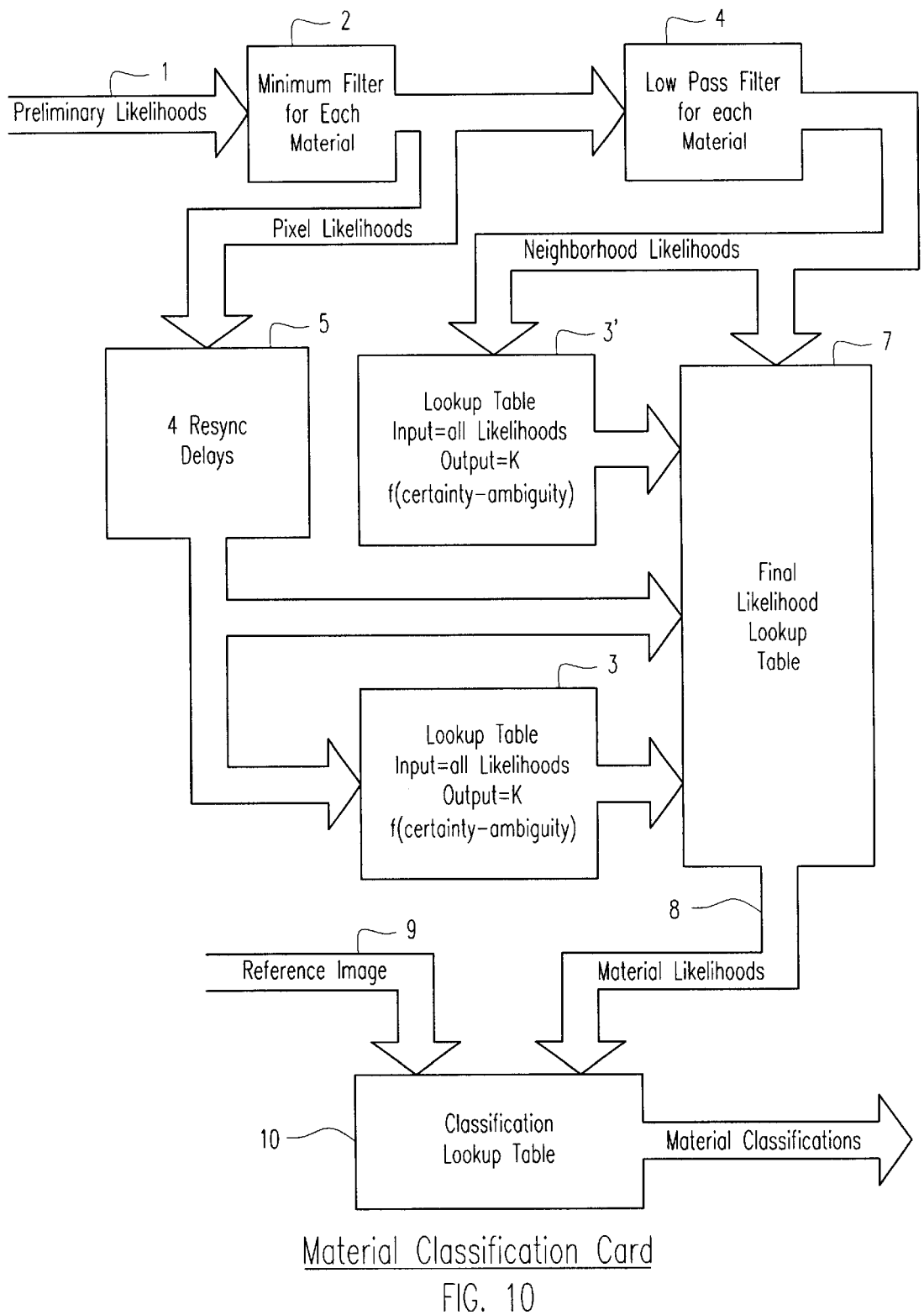
Figure 12:
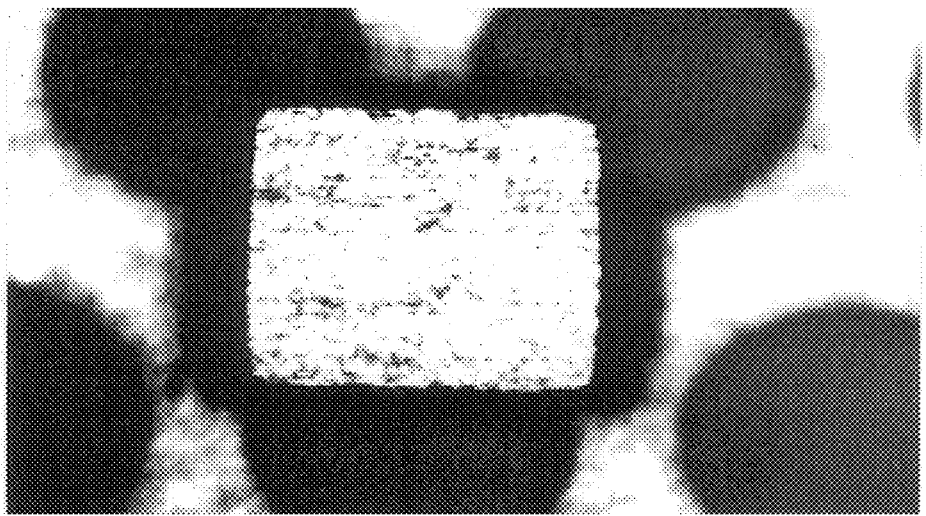
Figure 13:
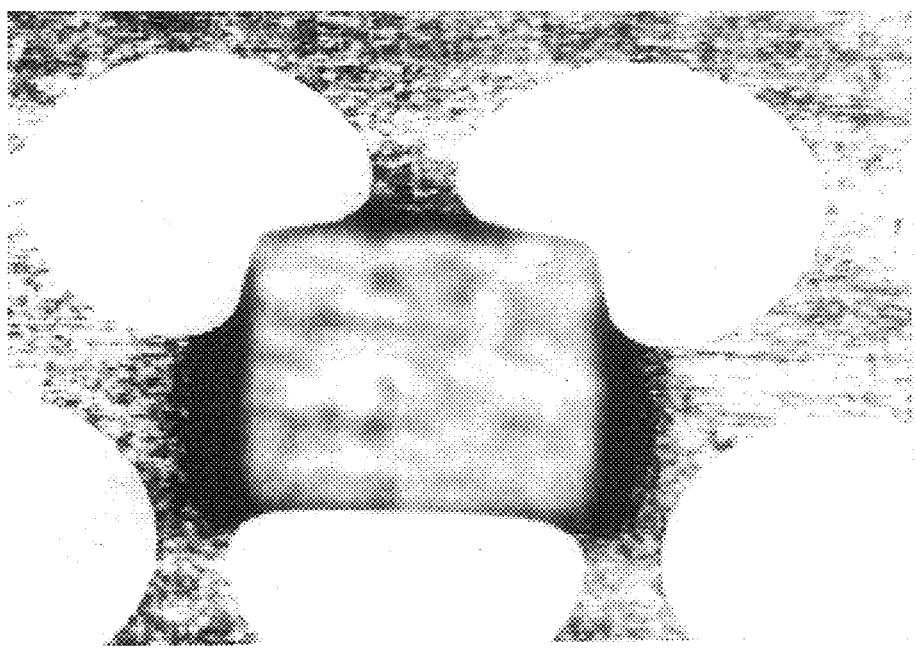
Figure 14:
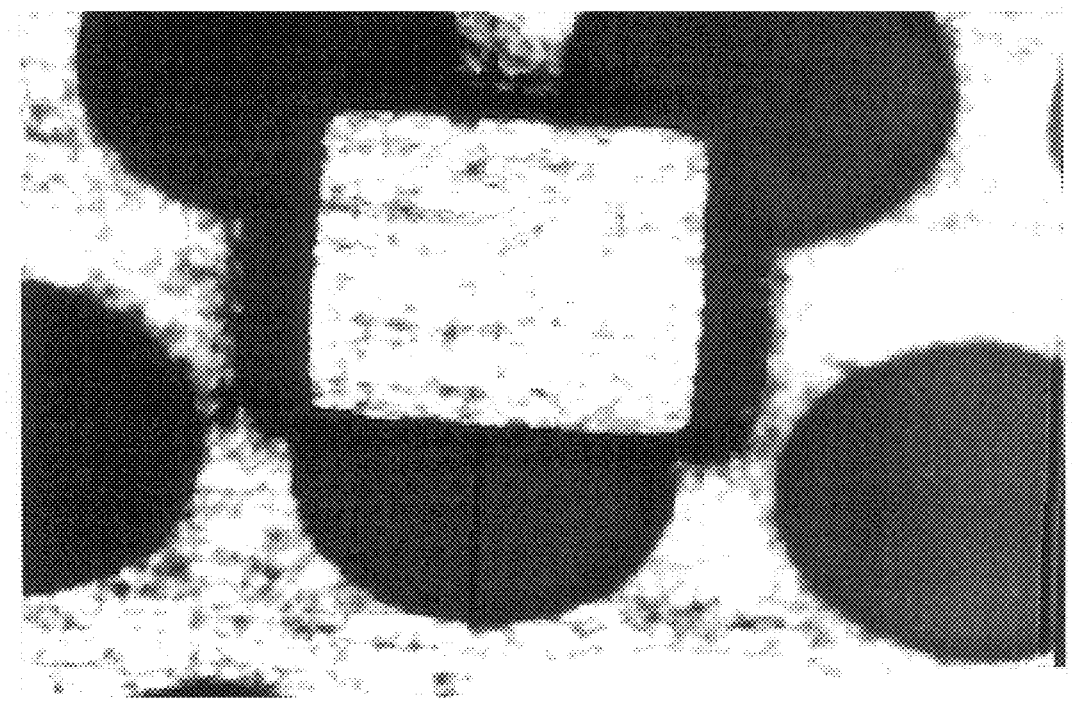
Figure 18:
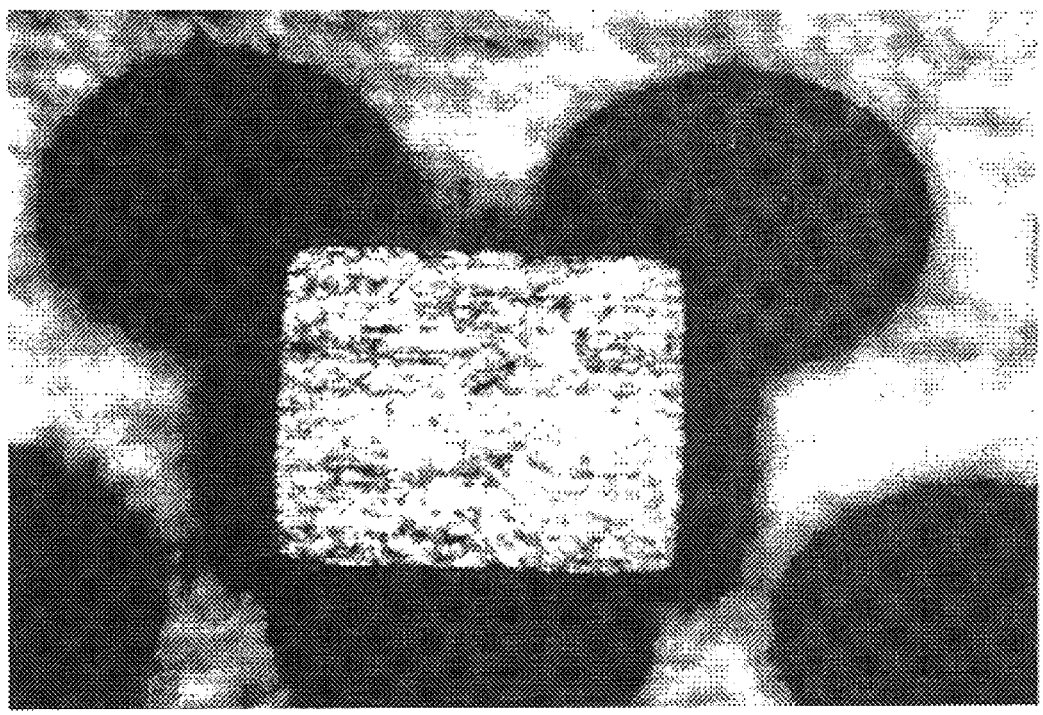
Figure 19:
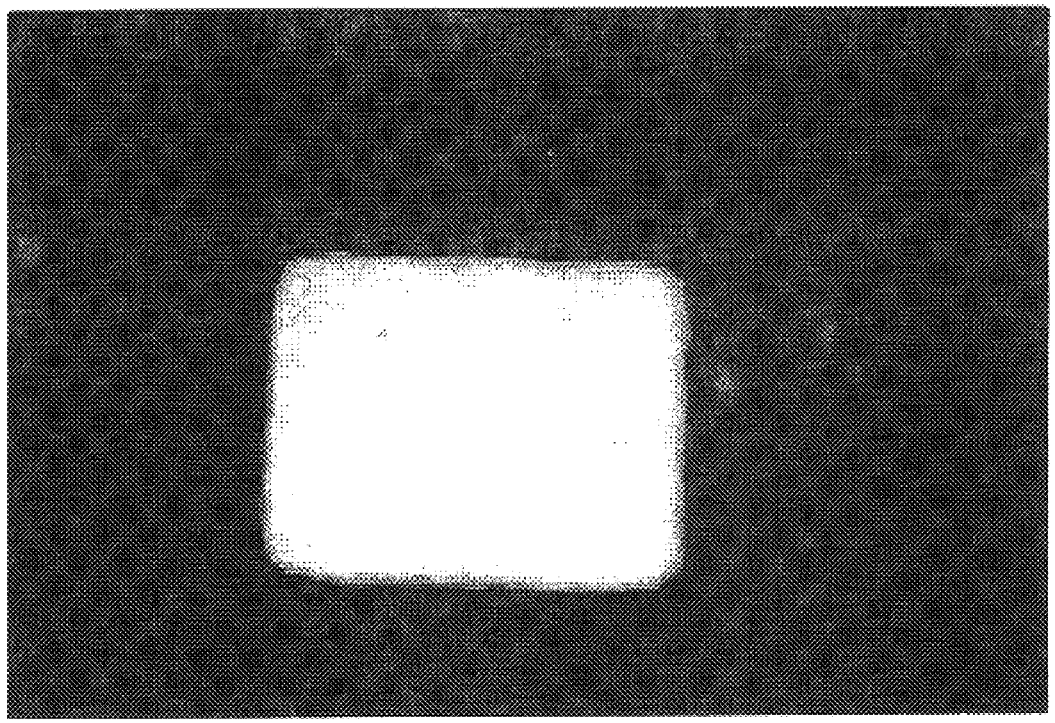
Figure 20:
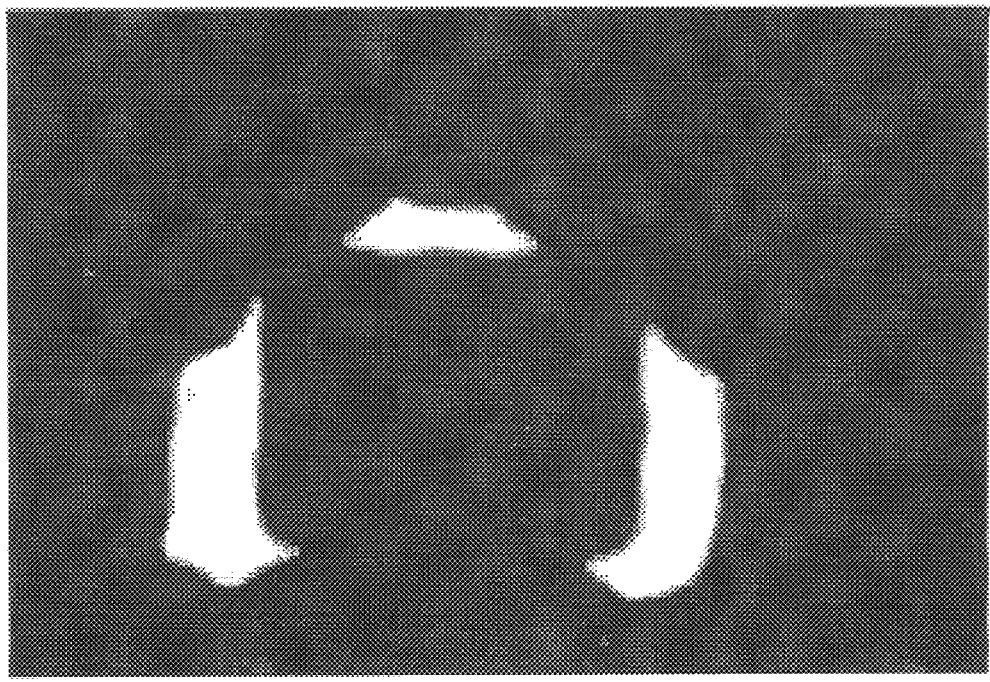
Figure 24:
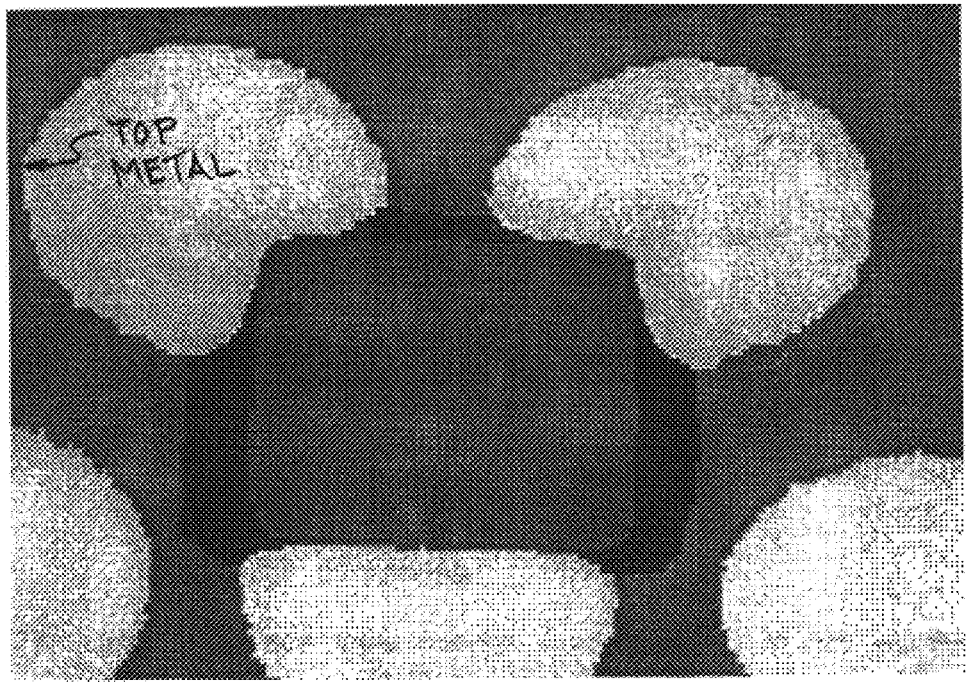
Figure 25:
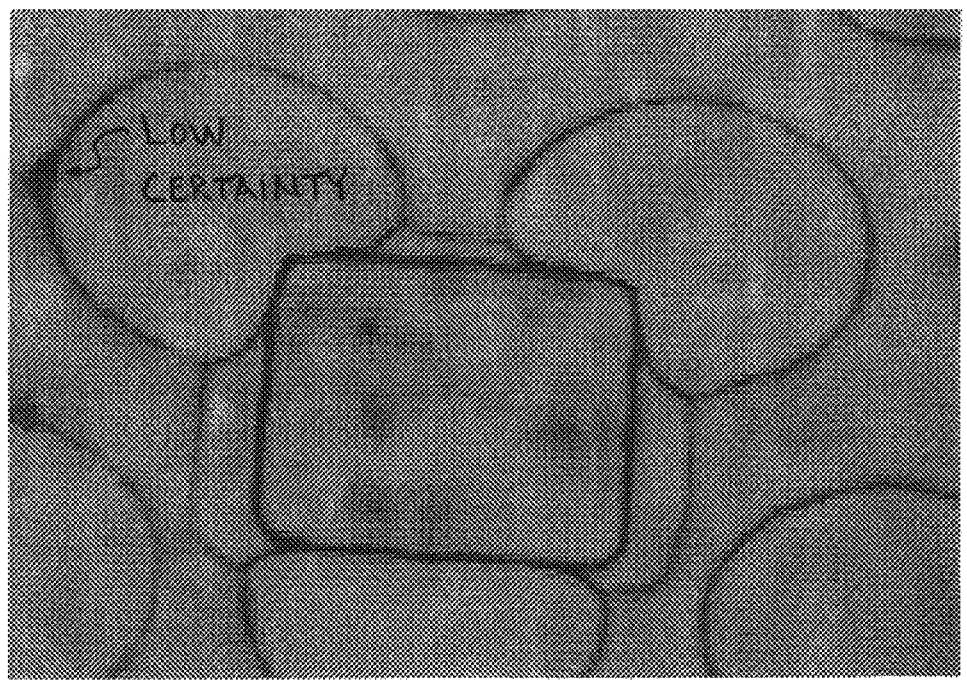
Figure 26:
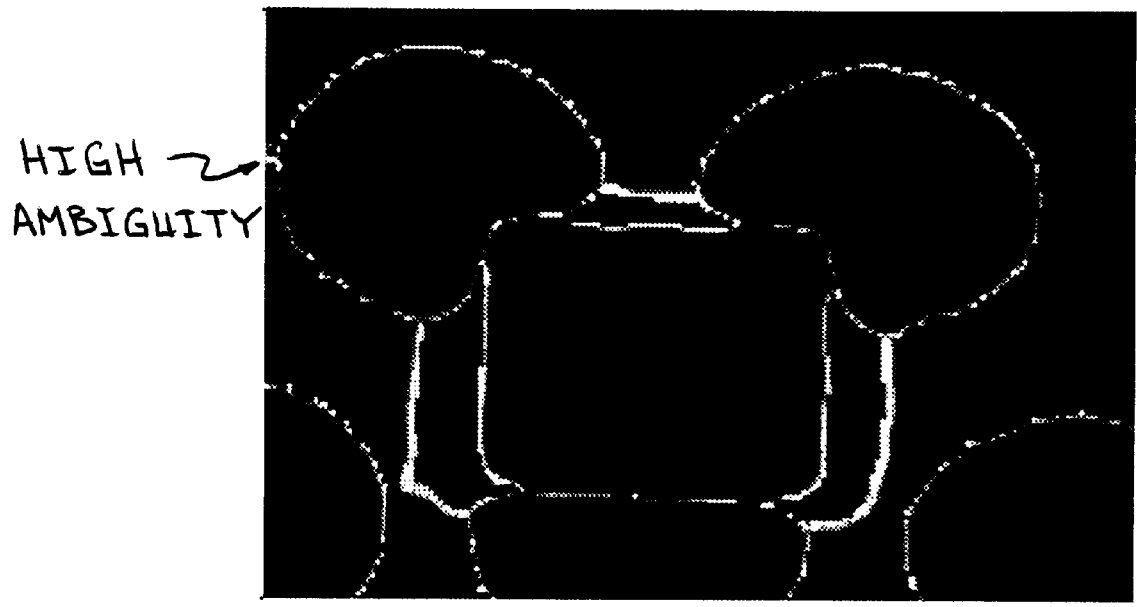

FIG. 10 is a diagram of a material classification card of the invention;

FIGS. 11 (a) and (b) are respectively 5×5 and 3×3 matrixes illustrating smoothing preliminary likelihoods;

FIGS. 12–14 are copies of photographs of images of top and bottom surfaces obtained in practice during the inspection of a multi-level highly textured metal mask for different focusing conditions;

FIGS. 15 and 16 are diagrams of different texture measurements for two different regions A and B;

FIG. 17 is a 2-camera system having a color, brightness and texture segmentation processing to produce four material likelihood indications;

FIG. 18 is an actually obtained image of an isolated top metal pad in the mask, and FIGS. 19–23 are actual likelihood images obtained for the four outputs of FIG. 17;

FIG. 24 shows a segmented image (the original images being shown in FIGS. 18 and 21) created by selecting for each spatial position of the image, the material with the greatest likelihood; and FIGS. 25 and 26 are respectively the certainty and ambiguity images for the segmented image of FIG. 24.

DESCRIPTION OF PREFERRED EMBODIMENT OF INVENTION

As before explained, the invention enables categorization of the different material regions of the optical image of the object-to-be-analyzed into given different materials by discriminating several different image characteristics—color, texture, brightness, and average brightness (in a highly textured area), and also by observing how a small region compares to the local neighborhood around it.

Figure 1:
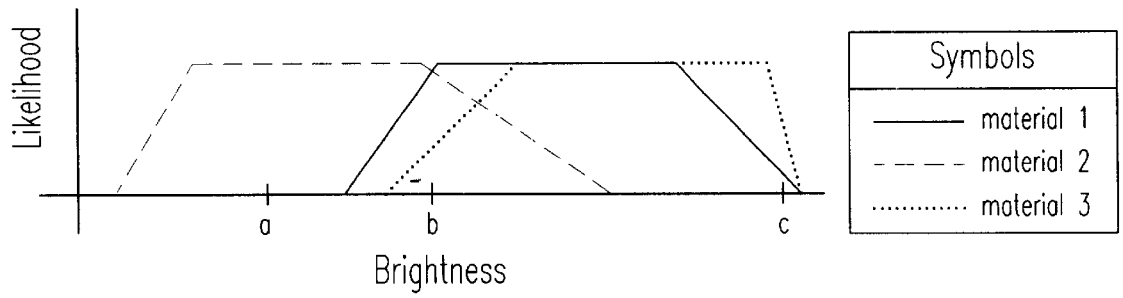

Each of these characteristics contributes to a likelihood value for each material. The likelihood value corresponds effectively to a degree of membership in a class. FIG. 1 shows a set of likelihood curves for three exemplary materials based on brightness. Based only on this characteristic, a fairly bright sample point has a high likelihood of being materials 1 (solid line) or 3 (dotted line), and is more a member of those classes than of material 2 (dashed line). The point has a certainty, which is equal to its highest likelihood. Also associated with each sample point is an ambiguity value, which is a measure of how distinguishable a material is relative to the other possible materials of choice. Ambiguity is computed as the ratio of the second most likely material likelihood to the most likely material likelihood at that point. When the highest likelihood is much higher than other likelihoods, the ambiguity is low; but when the likelihoods are closer together, the point is more ambiguous as to its material class. Again in FIG. 1, a point of brightness level "a" has a high likelihood for material 2, zero likelihoods for materials 1 and 3, a high certainty, and a low ambiguity; a point of brightness level "b" has high likelihoods for materials 1 and 2, a low likelihood for material 3, a high certainty, and a high ambiguity; and a point of brightness level "c" has low or zero likelihoods for all three materials and a low certainty, but still has a low ambiguity because the likelihood of material 3 is more than twice the likelihood of material 1.

Figure 2A:
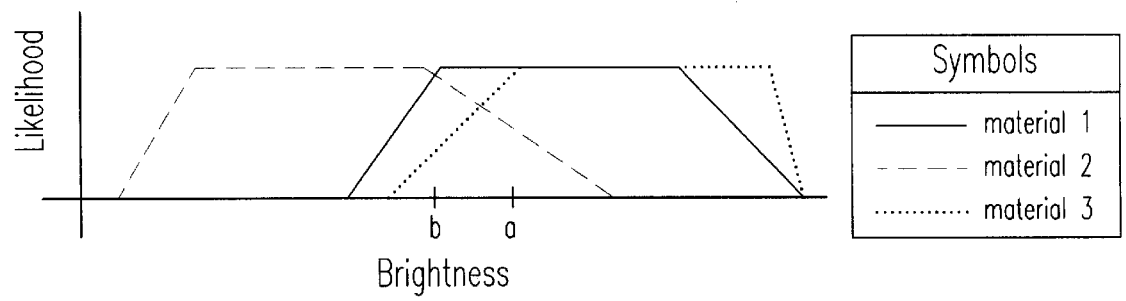
FIG. 2(a) is a similar graph for two such materials with different brightness levels and, FIG. 2(b), for different material textures.
Figure 2B:
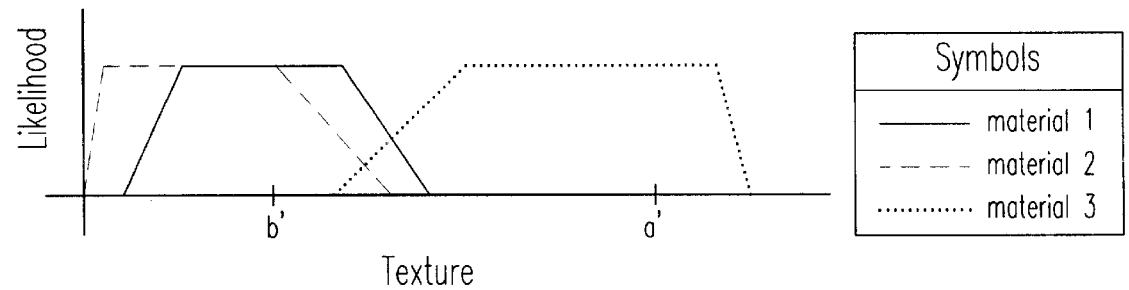

Factoring in one or more characteristics can lessen the ambiguity. In FIG. 2(a), for example, a point with brightness level "a" has high likelihoods for materials 1 and 3, but if it has a texture level a', it is much less ambiguous and more likely material 3. A point with brightness level b, however, has high likelihoods for materials 1 and 2; and if it has a texture level of b', FIG. 2(b), it is no less ambiguous. In such a case, considering more characteristics may reduce the ambiguity of the point.

A highly ambiguous point can be compared to its local neighborhood using a factor K; derived from the point ambiguity and its certainty. In FIG. 3, on the other hand, if the point "p" has high likelihoods for materials 1 and 2, and most of its local neighborhood is material 2, the point gains a higher likelihood for material 2. Using these altered likelihoods and a known reference image, thus, which provides a prior information of what material is expected at this location, the system categorizes each sample point.

GENERAL ARCHITECTURE OF THE INVENTION

To perform this categorization, the system must process the sample image, point by point. Characteristics such as brightness and color require information only about the point itself; but characteristics as texture and average brightness, require information from surrounding points as well. Points can therefore be compared to their surroundings both before and after preliminary likelihoods are assigned. The basic block to perform this function is a median filter, which, for each pixel, passes the median value of that pixel and its neighbors. (Configured differently, the filter can pass the minimum or maximum value of an area, as well.) Since it passes a median value instead of an average, an area of all black and white, for instance, FIG. 4(a), will still appear all black and white after processing as in FIG. 4(c), with the filter introducing no new levels, and without smearing boundaries.

FIG. 5 shows that images are fed from the inspection camera, so labeled, to the Material Analysis Card where, after processing to determine their characteristics, the pixels go to a lookup table that determines and assigns preliminary likelihoods for each possible material. In a two-camera system, as shown, which can collect images using two different color filters or from two different focal planes, the system then combines the likelihoods using more lookup tables, found on the Combine Card. The first and second of these tables compare the characteristics of the pixels from both cameras and assign likelihoods for those materials requiring information from both cameras, such as color or focal plane. The third of these tables then correlates the likelihoods from each camera and the likelihoods determined jointly from both cameras, to assign preliminary likelihoods for each material based on both images together. These preliminary likelihoods pass to the Material Classification Card, which determines ambiguity and the material likelihoods of each pixel's local neighborhood. It compares likelihoods and ambiguities of the pixel and its local neighborhood and combines this information with the a prior knowledge of what should be there as indicated by the reference image, to determine the material categorization of the pixel. The system passes these categorizations to other circuitry to check the sample for defects, as described, for example, in the previously cited patents.

Material Analysis Card

This card consists of median filters used to measure image values over a region, and lookup tables used to combine measured values and compute likelihood values. The filters are cascadeable spaced filters capable, as is known, of processing an arbitrarily large area. FIGS. 6(a)–(e) show how, by cascading two 3×3 spaced median filters, one can construct up to a 9×9 median filter. FIG. 7 presents a block diagram of the details of such a Material Analysis Card for use in the invention, including the cascadable filters and the delays needed for resynchronization. In the illustrative example of this figure, the system processes original pixel information, two arbitrary filter results (A and B), and a texture calculation.

The system can determine texture by calculating the absolute value of the difference of a pixel's brightness and the filtered brightness around it. As shown in FIG. 8, for example, regions or areas of high texture have a high absolute value of the difference between the brightness of individual pixels and the average brightness of the area. The system can filter this texture map, as by the illustrative 5×5 filtering of FIG. 8(b), to obtain an average measure of texture in a region by first locating areas of high texture using a maximum filter and then smoothing the results with a median filter (see block diagram FIG. 7).

The well-known use of adjustable delay lines on the inputs to the lookup tables ensures that all processed data is spatially and temporally aligned. The system first applies the original pixel and the processed filtered outputs to a set of lookup tables that produces preliminary likelihoods; and the system then assigns one value for each possible material at each pixel location. In a one-camera system, these preliminary likelihoods are applied directly to the Material Classification Card. A two-camera system, however, as in FIG. 5 before discussed, requires a Combine Card.

Combine Card

A two-camera system, as in FIG. 5, has two Material Analysis Cards, and the preliminary likelihoods from these cards must be combined into one likelihood set for the Material Classification Card, later discussed. The Combine Card accomplishes this by means of lookup tables, using not only the preliminary likelihood values but also the original and processed pixel information from the Material Analysis Cards. The card needs the pixel information in cases that require comparison of the camera images. Such cases include discriminating between colors or between focal planes on a bi-level system. To determine focal plane, for example, the system compares the texture images of the two cameras. Higher texture means better focus.

The Combine Card of FIG. 9 has three tiers of lookup tables to collate the preliminary likelihood values. FIG. 9 shows these tables for one material, using four distinct sets of pixel information: the original pixel and three processed sets, labeled Filter A, Filter B, and Filter C. The first tables take as inputs the original and filtered pixel information from both Material Analysis Cards and process them in pairs, resulting in combined pixel information, which passes to the second table. The second table takes this combined pixel information and assigns preliminary likelihoods, much the same way the lookup tables on the Material Analysis Card assign their preliminary likelihoods. The third lookup table takes in these combination preliminary likelihoods, along with the preliminary likelihoods from each of the Material Analysis Cards, and outputs the combined preliminary likelihood values, one per material, to the Material Classification Card.

Material Classification Card

Figure 11A:
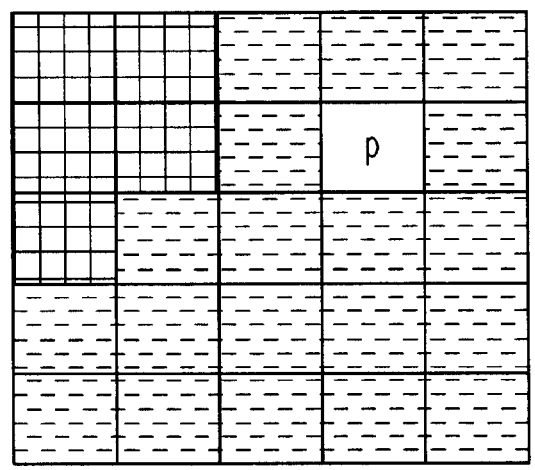
Figure 11B:
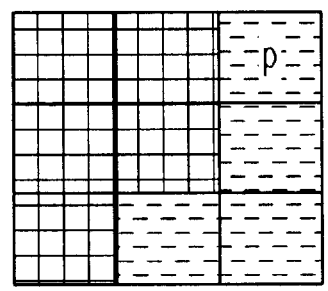

FIG. 10 shows a block diagram for such a Material Classification Card. This card calculates the certainty and ambiguity of each pixel, and uses that to determine a material for the pixel. The preliminary material likelihoods for each pixel at 1, pass through a minimum filter 2 to smooth away any single, isolated pixel with a higher likelihood than its immediate neighbors have. FIG. 11(a) shows a pixel p with a high (white) likelihood for a particular material for which its neighbors have only a low (black) or moderate (gray) likelihood. The 3×3 minimum filter smoothes the area, as shown in FIG. 11(b). The system of FIG. 10 then applies the modified likelihoods for all materials to a lookup table 3, out of which comes the factor K, which is a function of the pixel certainty minus its ambiguity, both of which are functions of the pixel's likelihoods. Meanwhile, the smoothed likelihoods also go through low-pass filters, one per material, which determine the material likelihoods of each pixel's local neighborhood. The system applies these regional neighborhood likelihoods to another lookup table 3' that produces the factor K for each pixel's neighborhood. Employing appropriate delays at 5, to achieve spatial and temporal alignment, the system resynchronizes these four items (pixel likelihoods, pixel Ks, neighborhood likelihoods, and neighborhood Ks) and applies them together to another lookup table 7. This table outputs the final material likelihoods for each pixel.

At this point, the system combines the final material likelihoods 8 with a priori information supplied by a known reference image 9. A lookup table 10 processes these bits into material classifications by comparing a pixel's final material likelihoods with the material classification of a known correct pixel. In this way, the system classifies each pixel of the sample into given material categories in order to inspect the sample for defects.

The manner, in which a prior reference information is incorporated to boost or attenuate likelihoods as a function of pixel position, enables the system to dynamically increase or decrease sensitivity to different types of defects, in real time, while scanning different regions of a part. For example, the texture, smoothness, or color of a part may be more critical in one spatial section of a part than in another, but both sections must be inspected to insure that material properties are within specified limits. The invention described herein can perform such dynamic inspection requirements.

The following illustrative example of the inspection of a multilevel, highly textured, metal mask with apparatus constructed and operated in accordance with the invention as above described, will now be detailed.

Metal masks contain the following types of material categories:

top metal surfaces bottom metal surfaces

Side wall transitions between top and bottom surfaces holes through the material The manner in which the invention, in actual practice, identifies each category through measuring and distinguishing selected features, is as follows.

Discriminating Top and Bottom Metal Surfaces

First, to discriminate the top and bottom metal surfaces, it has been determined that two cameras are required (FIG. 5) to differentiate top from bottom metal surfaces; one focused on the top surface the other on the bottom surface. FIGS. 12, 13 and 14 are actual images obtained from a top metal structure in the midst of a large bottom metal mesh area, with FIG. 12 obtained when focusing on the top surface; FIG. 13, when focusing on the bottom surface; and FIG. 14, by focusing half-way in between. FIG. 13 also shows holes illuminated from behind.

While in human inspection, the brain uses the in focus texture or texture difference to discriminate one layer from the other; with electronic optical imaging, the two layers cannot be readily distinguished when the camera is focused half-way between the layers as shown in FIG. 14.

As before indicated, it has been found that two camera's are essential to discriminate between these two surfaces. This was discovered by the following test, first performed on the assumption that the degree of texture perceived by a camera would always be greater when viewing the top surface with respect to the bottom surface over the entire part. Unfortunately, however, this assumption was found to be true only over small regions of the part. FIG. 15 shows the camera image obtained by viewing a top metal surface and an adjacent bottom surface in region A of the part. As for example, the in-focus texture measure for the top surface was 50 units as compared to only 20 units for the out-of-focus bottom surface. From this data one might conclude that a threshold of 35, halfway between these values, could be set to distinguish the two surfaces from one another. Texture measures greater than 35 units would imply top metal, while values less than 35 would imply bottom metal. To test this assumption, however, the part was moved to region B, and this experiment was repeated. The numbers measured were 90 units for the top surface and 60 units for the bottom surface. This would incorrectly classify both surfaces as top metal.

In accordance with the invention, it was found that the solution to this problem is to use two cameras and simultaneously compute the differential texture between the two cameras for each spatial position. If the camera focused on the top surface measures a higher texture than the camera focused on the bottom surface, then the material is most probably top metal. If the converse is true the material is most probably bottom metal.

Discriminating Holes from Glint

It was also initially assumed that one camera could distinguish holes from all other materials by illuminating the part using both reflected and transmitted light, and with the transmitted source substantially brighter than the top source. This would imply that any signal equal in brightness to the bright lower source would correspond to a hole through the material. It was found, however, that glint reflections off the top and bottom surfaces can be equally as bright, thereby disqualifying this means of classification.

The approach, described in this invention, rather, again takes advantage of the two-camera system, already required for top/bottom surface discrimination. Hole illumination is color coded in the frequency domain by a narrow band transmission filter placed in the lower illumination path. A second matched blocking or notch filter is placed in front of the camera focused on the top surface. As a result, holes image dark on the top surface camera and bright on the bottom surface camera as shown in FIGS. 12 and 13, while glint images are bright on both cameras.

Detecting Side Walls

Side walls exist on boundary transitions between top and bottom metal surfaces and correspond to rapid changes in topological height. Their presence within a large top metal region is indicative of pits and surface defects. They are characterized by dark areas of low texture and are primarily detected by measuring the brightness and texture of a region.

The Learning Procedure

The system is initially shown images containing the before-listed different types of feature categories or materials that it is expected to identify for metal masks; i.e. the four material categories of top and bottom surfaces, sidewall transitions therebetween and holes through the material.

During the learn phase, the system is shown sample images for each of these four categories. Brightness, texture, and color characteristics are automatically extracted from each image and used as a material discriminator. Depending upon the degree of process variation between samples, the system can be taught new characteristics, in the manner described in the earlier cited patens or as is otherwise known, once per part, once per lot, once per week, once per year or any combination thereof. Teaching only requires taking snap shots of each material at known locations of the part. These locations can be entered into the system as part of the normal setup procedure Image Segmentation and Material Analysis The first phase of the inspection process is to segment the image into material categories using the learned brightness, color and texture characteristics to determine the most likely material at each point in the image. The color-brightness-texture segmentation module shown in FIG. 17, containing four processing choices which each independently calculates the likelihood that a point belongs to a given category. For this example, the point is classified as the material with the greatest likelihood that does not exceed ambiguity limits. Defects are detected, as also discussed in said patents, at a later stage in the process by detecting an incorrect material at a given location.

FIG. 18 is an actual image obtained in practice of an isolated top metal pad in a multi-layer structure, and FIGS. 19 through 23 are actual likelihood images corresponding to the four outputs shown in FIG. 17. The intensity at each spatial location is proportional to the likelihood. The brighter the point, the higher the likelihood of the given material. The segmented image shown in FIG. 24 is created by selecting, for each spatial position of the image, the material with the greatest likelihood.

Defect Detection and Material Classification

Defects, as before stated, are detected at a later stage in the machine operation, as incorrect material greater than a minimum size present at a given location. The accuracy of the segmentation process can be greatly improved by introducing two new measurements before referred to as certainty and ambiguity. The certainty is equal to the likelihood of the selected material and the ambiguity is the ratio of the second most likely material divided by the likelihood of the most probable material. The importance of these two new measures is illustrated by the following three examples:

EXAMPLE 1 likelihood (top metal or material 1) = 75 units
likelihood (bottom metal or material 2) = 15 units
likelihood (side wall or material 3) =7 units
likelihood (hole or material 4) =4 units
classification: top metal or material 1
certainty = 75 units
ambiguity = 15/75 = 0.2 units Conclusion: One can be reasonably certain that the material has been correctly classified as top metal or material 1 since there are no other close contenders (low ambiguity) and the certainty value is relatively high.

EXAMPLE 2 likelihood (top metal or material 1) = 50 units
likelihood (bottom metal or material 2) = 55 units
likelihood (side wall or material 3) = 7 units
likelihood (hole or material 4) = 4 units
classification: bottom metal or material 2
certainty = 55 units
ambiguity = 50/55 = 0.91 units Conclusion: One cannot be certain whether this material is really bottom metal or material 2 since the ambiguity is so high. It may be discolored top metal or damaged material 1. Under such conditions it may be best, in accordance with the methodology of the invention, to examine its neighbors prior to declaring it an actual defect.

EXAMPLE 3 likelihood (top metal or material 1) = 5 units
likelihood (bottom metal or material 2) = 45 units
likelihood (side wall or material 3) = 7 units
likelihood (hole or material 3) = 4 units
classification: bottom metal or material 2
certainty = 45 units
ambiguity = 7/45 = 0.15 units Conclusion: This material is most probably classified correctly since there are no close contenders (ambiguity is low). The somewhat lower certainty probably indicates that the metal or material 2 finish has been discolored and does not precisely match the characteristics of normal bottom metal or material 2.

EXAMPLE 4 likelihood (top metal or material 1) = 5 units
likelihood (bottom metalor material 2) = 15 units
likelihood (side wall or material 3) = 7 units
likelihood (hole or material 3) = 4 units
classification: unknown material
certainty = 15 units
ambiguity = 7/15 = 0.46 units Conclusion: This material is unknown due to its low certainty and is classified as a defect. It is most probably foreign material or contamination.

Figure 21:
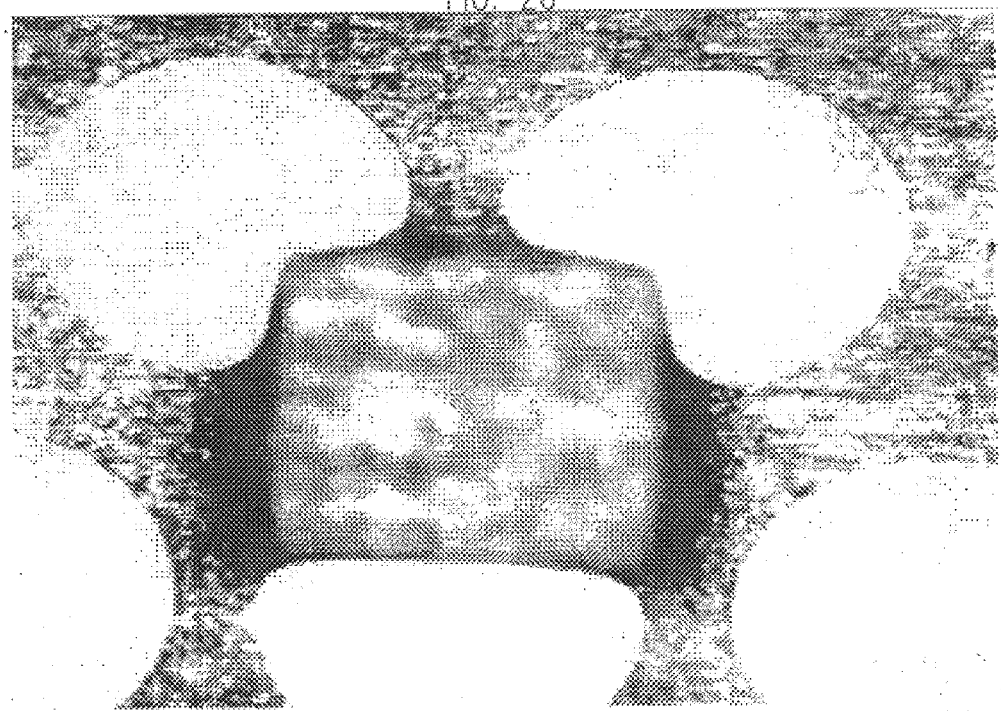
Figure 22:
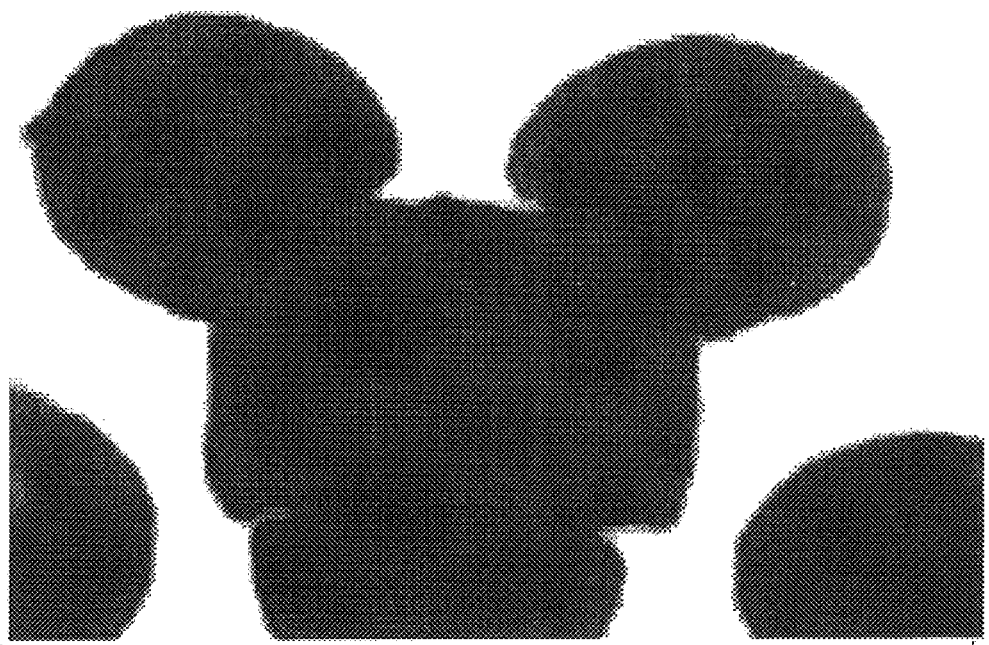
Figure 23:
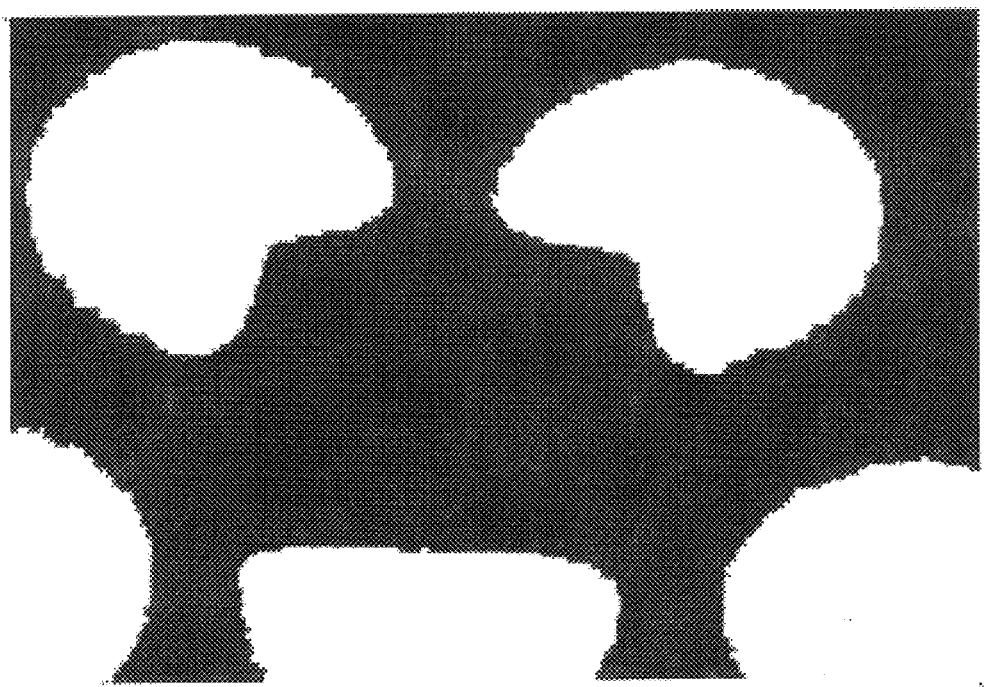

FIGS. 25 and 26 are the certainty and ambiguity images respectively for the segmented image shown in FIG. 24 (with the original camera images being shown in before-discussed FIGS. 18 and 21). It should be noted that the segmented image of FIG. 24 contains a small red spot, indicative of top metal, on a hole/bottom metal boundary on the left side of the image. Since this spot is extremely small, has low certainty (FIG. 25) and high ambiguity (FIG. 26), the spot can be ignored and would not be considered to constitute a valid defect.

Other Applications Of The Invention

The present invention described herein can also be used to implement the image processing algorithms described in the two previous referenced patents. U.S. Pat. No. 5,524,152 "Method of and apparatus for object or surface inspection employing multicolor reflection discrimination" discloses a technique wherein color signals generated by two different color cameras are multiplied by specific coefficients and with summing of the result. The magnitude and sign of the result is used to discriminate between samples. The Combine Card described herein can usefully be employed to compute this computation.

In the system of the other U.S. Pat. No. 5,119,434, "Method of and Apparatus for Increasing the Processing Speed in the Scanning Inspection of Circuit Boards and Other Objects"; processing speed is intelligently increased by reducing the number of data points needed to inspect a sample by a predetermined factor, preferably of four. This is achieved by sub-sampling the data to eliminate redundant information. The neighborhood around each pixel is analyzed to determine if it sufficiently deviates from its neighbors to constitute a defect; if not, a single pixel is produced for each group of four input pixels. This single pixel reflects the average value of the group. If the neighborhood does contain a pixel which does look like a defect, the single pixel output is set to the value of the defect, thereby preserving the defect in the data-reduced, sub-sampled output. This algorithm can also usefully be implemented in the present invention, with the neighborhood processor and lookup tables easily programmed to implement this function.

Further modifications and uses of the present invention and features therof will also occur to others skilled in the art, and such are considered to fall within the spirit and scope of the invention as defined in the appended claims.

What is claimed is:

1. A method of categorizing different material regions of an object-to-be-inspected, that comprises, optically scanning the object to produce a pixel image thereof; discriminating different pixel regions of the image corresponding to possibly different materials on the basis of color and brightness measurements of the pixel regions and assigning preliminary likelihoods to such discrimination though with ambiguities; and comparing the measurements of the pixel regions with their local neighborhood surroundings in the image to assist in resolving said ambiguities and to determine the materials categorization of the pixel regions with a higher likelihood.

2. The method of claim 1 wherein said pixel regions are also compared with a reference image further to aid in the resolution of said ambiguities.

3. The method of claim 1 wherein the pixel regions are also discriminated on the basis of texture of image regions.

4. The method of claim 3 wherein, in a highly textured area, discrimination is effected on the basis of average brightness measurement.

5. A method of categorizing different material regions of an object-to-be-inspected, that comprises, optically scanning the object to produce a pixel image thereof; discriminating different pixel regions of the image corresponding to possibly different materials on the basis of color and brightness measurements of the pixel regions and assigning preliminary likelihoods to such discrimination though with ambiguities; and comparing the measurements of the pixel regions with their local neighborhood surroundings in the image to assist in resolving said ambiguities and to determine the materials categorization of the pixel regions with a higher likelihood, wherein values of ambiguity are established to distinguish the different material regions from one another, the values being computed as the ratio of the second most likely assigned material likelihood to the most likely assigned material likelihood at that region.

6. The method of claim 5 wherein certainty values for region material likelihoods are assigned representing the highest likelihood for that region.

7. Apparatus for categorizing different material regions of an object-to-be-inspected having, in combination, an optical scanning camera system for inspecting and scanning successive regions of said object to produce pixel images thereof; means for measuring the color and brightness of characteristics of the successive pixel image regions to discriminate possibly different materials thereof, assigning preliminary likelihoods of their being such different materials, with ambiguities; and means for comparing the measurements of the pixel regions with their local neighborhood surroundings in the image and with a reference image, to assist in resolving said ambiguities and determining materials categorization of the pixel regions with a higher likelihood.

8. The apparatus claimed in claim 7 wherein color and brightness characteristics measuring means receives scanned image information from the pixel regions, and further measuring means is provided for processing information such as texture and average brightness characteristics from the surrounding local neighborhood of the regions and for comparing the same.

9. The apparatus claimed in claim 8 wherein said likelihood assigning is effected either before or after comparing the regions to their surrounding local neighborhood.

10. The apparatus claimed claim 9 wherein said comparing is effected by median filter means which, for each pixel, passes the median value of that pixel and its neighborhood measurements.

11. The apparatus claimed in claim 8 wherein means is provided for teaching and entering into the apparatus images of expected feature and material categories for reference in comparing with the likelihoods derived from brightness, color and texture characteristic measurements.

12. The apparatus claimed in claim 11 wherein means is provided for segmenting the image into material categories using the learned reference brightness, color and texture characteristics to determine the most likely material at each point of the image, classifying the material on the basis of the greatest likelihood that does not exceed ambiguity limits.

13. The apparatus claimed in claim 12 wherein the image segmenting means provides an image point intensely at each spatial location that is proportional to its measured likelihood, with the brighter the point, the higher the likelihood of the given material.

14. The apparatus claimed in claim 13 wherein means is provided for improving that accuracy of the segmentation process by providing measurements of certainty equal to the likelihood of the selected material, and ambiguity equal to the ratio of the second most likely material divided by the likelihood of the most probable material.

15. The apparatus claimed in claim 14 wherein means is provided for creating images of the certainty and ambiguity measurements for the segmented image, to aid and detect, such as an incorrect material that is greater than a predetermined minimum size at a given location.

16. The apparatus claimed in claim 15 wherein the object is a multilevel, highly textured metal mask having material categories of top and bottom metal surfaces, side wall transitions there-between, and holes through the material, the material likelihoods of each of which are obtained with certainty and ambiguity values.

17. The apparatus claimed in claim 7 wherein said pixel images are fed from the camera system to a material analysis card for processing to determine the measurements of said characteristics and to compare the same with a reference look-up table that determines and assigns said preliminary likelihoods.

18. The apparatus claimed in claim 7 wherein said scanning camera system comprises two cameras adapted to collect images of the object either from two different color filters or from two different focal planes.

19. The apparatus claimed claim 18 wherein a combine card is provided having a plurality of reference look-up tables with means for comparing said characteristics of the pixel images from both cameras and assigning material likelihoods those materials requiring information from both cameras, such as color and focal plane.

20. The apparatus of claim 19 wherein said combine card is provided with a further reference look-up table for enabling correlation of the likelihoods from each camera and the likelihoods determined jointly from both cameras and assigning preliminary likelihoods for each material based on both camera images together.

21. The apparatus of claim 20 wherein a material classification card is further provided for comparing likelihoods and ambiguities of the regions and their respective local neighborhood and for combining such information with predetermined information of said reference image, thereby to determine the material categorization of the region with higher likelihood.

22. The apparatus of claim 21 wherein means is provided for passing the material categorization information to defect monitoring circuitry.

23. The apparatus of claim 21 wherein the material analysis card comprises median filters for measuring image values over regions, and lookup tables used to combine measured values and composite likelihood values.

24. The apparatus of claim 23 wherein the filters are cascadable spaced filters adapted to process in arbitrarily large area, with delay lines associated with the look-up tables for enabling resynchronization.

25. The apparatus of claim 24 wherein image region texture is determined by means for calculating the absolute value of the difference between the brightness of a pixel in the image and the filtered average brightness around it.

26. The apparatus of claim 25 wherein said average brightness is obtained by means for locating areas of high texture and applying the same to a maximum filter and to a smoothing median filter.

27. The apparatus of claim 25 wherein said delay lines are adjustable and insure that all processed data inputted to look-up tables is spatially and temporarily aligned, with the original image pixel and the processed filtered output first being assigned preliminary likelihoods with look-up tables, and then assigning one value to each possible material at each pixel location.

28. The apparatus is claimed in claim 23 wherein the material classification card is provided with means for calculating the certainty and ambiguity of each image pixel and using such to determine the material for that pixel.

29. The apparatus as claimed in claim 28 wherein preliminary material likelihoods for each pixel are passed through a minimum filter to smooth away any single isolated pixel with a higher likelihood than that of its immediate neighbors.

30. The apparatus as claimed in claim 29 wherein the minimum filter likelihood outputs for all materials are applied to a first look-up table for determining a factor K which is a function of the pixel certainty minus its ambiguity, wherein both the pixel certainty and ambiguity are functions of the pixel likelihood valued.

31. The apparatus as claimed in claim 30 wherein the minimum filter likelihood outputs are also fed through low-pass filters, one per material, to determine the material likelihoods of the local neighborhood of each pixel.

32. The apparatus as claimed in claim 31 wherein means is provided for applying the local neighborhood likelihoods to a further look-up table to produce factors K for each pixel neighborhood.

33. The apparatus as claimed in claim 32 wherein delay means are provided to achieve spatial and temporal alignment to enable the apparatus to resynchronize all of the pixel likelihoods, the pixel K's, neighborhood likelihoods and the neighborhood K's, and to apply them together to another look-up table for out-putting the final material likelihoods for each pixel.

34. The apparatus of claim 33 wherein means is provided for combining the last-named table outputs of final material likelihoods with a prior information from a known reference image, and, with a further look-up table, comparing each pixel's final material likelihoods with material classification of a known correct pixel, enabling classification of each pixel of the object into given material categories.

35. The apparatus of claim 34 wherein means is provided for supplying the material category information to defect inspection circuits.

36. The apparatus of claim 18 wherein the cameras are differently focused upon different regions of the object, such as top and bottom surfaces, and means is provided for simultaneously computing the differential image texture received by the two cameras for the regions.

37. The apparatus claimed in claim 36 wherein the object is provided with one or more holes and bottom illumination therethrough supplementing top illumination for the two-camera imaging, and means is provided for differentiating glint images through imaging holes dark on the camera focused on the top surface and bright on the bottom surface.

38. The apparatus claimed in claim 36 wherein means is provided for detecting boundary transition regions such as side walls between the top and bottom surfaces of the object by measuring the brightness and texture of such transition regions to determine dark areas of low texture that characterizes the images of such regions.

39. Apparatus for categorizing different material regions of an object-to-be-inspected having, in combination, an optical scanning camera system for inspecting and scanning successive regions of said object to produce pixel images thereof; means for measuring the color and brightness of characteristics of the successive pixel image regions to discriminate possibly different materials thereof, assigning preliminary likelihoods of their being such different materials, with ambiguities; and means for comparing the measurements of the pixel regions with their local neighborhood surroundings in the image and with a reference image, to assist in resolving said ambiguities and determining materials categorization of the pixel regions with a higher likelihood, wherein said scanning camera system comprises two cameras adapted to collect images of the object either from two different color filters or from two different focal planes, and wherein a combine card is provided having a plurality of reference look-up tables with means for comparing said characteristics of the pixel images from both cameras and assigning material likelihoods to those materials requiring information from both cameras, such as color and focal plane, wherein said combine card is provided with a further reference look-up table for enabling correlation of the likelihoods from each camera and the likelihoods determined jointly from both cameras and assigning preliminary likelihoods for each material based on both camera images together; and wherein a material classification card is further provided for comparing likelihoods and ambiguities of the regions and their respective local neighborhoods and for combining such information with predetermined information of said reference image, thereby to determine the material categorization of the region with higher likelihood, and wherein the material analysis card comprises median filters for measuring image values over regions, and lookup tables used to combine measured values and composite likelihood values, the filters being cascadable spaced filters adapted to process in arbitrarily large area, with delay lines associated with look-up tables for enabling resynchronization.

* * * * *